United States Patent
Han et al.

(10) Patent No.: US 8,846,974 B2
(45) Date of Patent: Sep. 30, 2014

(54) MOLYBDENUM-CONTAINING ACIDIC CATALYSTS TO CONVERT CELLULOSIC BIOMASS TO GLYCOLIC ACID

(71) Applicant: King Abdullah University of Science and Technology, Thuwal (SA)

(72) Inventors: Yu Han, Thuwal (SA); Jizhe Zhang, Thuwal (SA); Xin Liu, Thuwal (SA)

(73) Assignee: King Abdullah University of Science and Technology, Thuwal (SA)

(*) Notice: Subject to any disclaimer, the term of this patent is extended or adjusted under 35 U.S.C. 154(b) by 55 days.

(21) Appl. No.: 13/859,887

(22) Filed: Apr. 10, 2013

(65) Prior Publication Data

US 2013/0281733 A1    Oct. 24, 2013

Related U.S. Application Data

(60) Provisional application No. 61/622,170, filed on Apr. 10, 2012.

(51) Int. Cl.
| | |
|---|---|
| *C07C 227/00* | (2006.01) |
| *B01J 27/19* | (2006.01) |
| *B01J 23/30* | (2006.01) |
| *B01J 23/28* | (2006.01) |
| *B01J 27/188* | (2006.01) |
| *C07C 51/00* | (2006.01) |
| *C07C 51/31* | (2006.01) |

(52) U.S. Cl.
CPC ............... *C07C 51/00* (2013.01); *B01J 27/19* (2013.01); *B01J 23/30* (2013.01); *B01J 23/28* (2013.01); *B01J 27/188* (2013.01); *C07C 51/313* (2013.01)
USPC .......................................................... 562/516

(58) Field of Classification Search
CPC .. C07C 227/00; C07C 51/353; C07C 319/20; C07C 229/36; C07C 233/47
See application file for complete search history.

(56) References Cited

U.S. PATENT DOCUMENTS

2011/0319672 A1    12/2011 Liu et al.

OTHER PUBLICATIONS

Tian, et al., "Hydrolysis of Cellulose by the Heteropoly Acid H3PW12O40", Cellulose, 2010, vol. 17, p. 587-594.
Shimizu, et al., "Effects of Brønsted and Lewis acidities on activity and selectivity of heteropolyacid-based catalysts for hydrolysis of cellobiose and cellulose", Green Chemistry, 2009, vol. 11, p. 1627.
Ogasawara, et al.,"Saccharification of natural lignocellulose biomass and polysaccharides by highly negatively charged heteropolyacids in concentrated aqueous solution", ChemSusChem, Apr. 18, 2011, vol. 4, pp. 519-525.
Swatloski, et al., "Dissolution of Cellose with Ionic Liquids", Journal American Chemical Soceity, Apr. 17, 2002, vol. 124, No. 18, pp. 4974-4975.
Bridgwater, et al., "Fast pyrolysis processes for biomass", Renew. Sust. Energ. Rev. 2000, vol. 4, Issue 1, pp. 1-73.

(Continued)

*Primary Examiner* — Rosalynd Keys
*Assistant Examiner* — Jennifer C Sawyer
(74) *Attorney, Agent, or Firm* — Fulbright & Jaworski LLP

(57) ABSTRACT

Embodiments of the present invention include methods and compositions related to catabolic conversion of cellulosic biomass to glycolic acid using molybdenum-containing acidic catalysts. The invention includes the use of heteropoly and isopoly acids and salts as the molybdenum-containing multi-functional catalysts for biomass conversion. In embodiments of the invention, the reactions employ successive hydrolysis, retro-aldol fragmentation, and selective oxidation in a noble metal-free system.

12 Claims, 3 Drawing Sheets

(56) References Cited

OTHER PUBLICATIONS

Ji, et al., "Direct Catalytic Conversion of Cellulose into Ethylene Glycol Using Nickel-Promoted Tungsten Carbide Catalysts", Angew. Chem.-Int. Ed. 2008, vol. 47, pp. 8510-8513.

Matson, et al., "One-pot catalytic conversion of cellulose and of woody biomass solids to liquid fuels", Journal American Chemical Society, 2011, vol. 133, No. 35, pp. 14090-14097.

Holm, et al., "Conversion of sugars to lactic acid derivatives using heterogeneous zeotype catalysts", Science 2010, vol. 328, pp. 602.

Zhang, et al., "Highly Selective and Complete Conversion of Cellobiose to Gluconic Acid Au/Cs2HPW12O40 Nanocomposite Catalyst", ChemCatChem 2011, vol. 3, pp. 1294-1298.

Zhang et al., "Direct Conversion of Cellulose to Glycolic Acid with a Phosphomolybdic Acid Catalyst in a Water Medium", ACS Catal., 2012, vol. 2, No. 8, pp. 1698-1702.

¹H NMR

¹³C NMR

MOLYBDENUM-CONTAINING ACIDIC CATALYSTS TO CONVERT CELLULOSIC BIOMASS TO GLYCOLIC ACID

This application claims priority to U.S. Provisional Patent Application Ser. No. 61/622,170, filed on Apr. 10, 2012, which is incorporated by reference herein in its entirety.

TECHNICAL FIELD

The present invention concerns at least the fields of chemistry, biochemistry and the life sciences. In particular aspects the field concerns conversion of cellulosic biomass to glycolic acid using molybdenum-containing acidic catalysts.

BACKGROUND OF THE INVENTION

Cellulosic biomass is an abundant and sustainable natural resource. Its efficient utilization has long been the focus of research and development efforts with the aim to compete with and replace petroleum-based products. In addition to the production of bio-fuels (e.g., ethanol) that has proven to be successful,[1-4] the conversion of cellulosic biomass to high value-added chemicals is equally important.[5-9] In comparison with the conventional fermentation processes, catalysis would provide a greener and more cost-efficient route for producing chemicals of commercial interest from biomass.[4] There have been numerous studies on catalytic conversions of various carbohydrates to useful compounds or important chemical intermediates. For example, sorbitol and gluconic acid were produced from glucose or cellobiose by catalytic hydrogenation and oxidation respectively;[10-13] 5-hydroxymethylfurfural (5-HMF) and levulinic acid were prepared by catalytic dehydration of different carbohydrates;[14-17] methyl lactate was derived with high yield from sucrose, glucose and fructose using Sn-doped Lewis acidic zeolite catalyst;[18] catalytic isomerization between fructose and glucose has also been studied.[19,20] Despite the great success achieved with small-molecule biomass derivatives (e.g. mono- and disaccharides), the direct catalytic conversion of cellulose is still a challenge, mainly because cellulose is highly stable and insoluble in most solvents. To overcome this problem, ionic liquids are usually used as solvent for their special ability to dissolve cellulose,[21-23] or alternatively extreme conditions are applied to facilitate the reactions.[5,24-26]

Heteropoly acids (HPAs) have been used for cellulosic biomass conversion, where the function of HPA is to catalyze the hydrolysis of cellulose and the products are limited to glucose and fructose.[27-29] US Patent Application Publication No. 20110257448 and US Patent Application Publication No. 20110009614 disclose that HPA-supported noble metal catalysts can be used to convert biomass-derived oxygenated hydrocarbons to sugar alcohols and hydrocarbons through hydrogenation reactions. The inventors of the present invention recently reported a novel composite catalyst, cesium hydrogen phosphotungstate-supported Au (Au/$Cs_2HPW_{12}O_{40}$), for highly selective and complete conversion of a disaccharide (cellobiose) to gluconic acid, where the phosphotungstate and Au nanoparticles provide solid acid sites for hydrolysis and redox sites for selective oxidation respectively[11]. However, using HPAs (without noble metal) as catalysts to produce chemicals of commercial interest from cellulosic biomass materials via successive hydrolysis and selective oxidation has not been reported in literatures. In particular, the direct production of glycolic acid, an important compound widely used in organic synthesis, biodegradable polymer synthesis, skin-care products, industrial rust removal and food processing, from cellulosic biomass materials has not been achieved.

BRIEF SUMMARY OF THE INVENTION

The present invention is directed to systems, methods, and compositions that concern conversion of cellulosic biomass to glycolic acid utilizing molybdenum-containing acidic catalysts.

Embodiments of the invention result in the production of glycolic acid, which is an important compound widely used in organic synthesis, biodegradable polymer synthesis, skin-care products, and food processing, for example. Glycolic acid may be produced in methods of the invention from various cellulosic biomass feedstock including cellulose, wood pulp, cotton, starch, lignin, bagasse, grass and various mono- and disaccharides.

In specific embodiments of the invention, there is the catalytic production of glycolic acid directly from cellulosic biomass.

In some embodiments, Mo-containing acidic catalysts (HPAs, IPAs and oxides) are utilized for biomass conversion.

In specific embodiments of the invention, the methods employed herein are in contrast to those for using certain HPAs for cellulose conversion in which the function of HPAs is only to catalyze the hydrolysis of cellulose, and the products are glucose and fructose. In contrast, aspects of the present invention provide Mo-containing catalysts that are multi-functional by being able to catalyze the hydrolysis of cellulose, the fragmentation of the obtained hexoses and the oxidation of the produced shorter carbohydrates, with the product being glycolic acid. Such "multi-functionality" distinguishes the inventive use of Mo-containing acidic catalysts from previously used catalysts for biomass conversion and leads to the production of glycolic acid.

In embodiments of the invention, there is catalysis for biomass conversion, and in comparison with conventional fermentation processes, catalysis provides a greener and more cost-efficient route for producing chemicals of commercial interest from biomass.

In certain embodiments of the invention, there is direct conversion of cellulose to glycolic acid with phosphomolybdic acid catalyst in water media.

In some embodiments of the invention, there is a method of converting cellulosic biomass materials to glycolic acid, comprising the steps of reacting one or more cellulosic biomass materials with molybdenum-containing acidic catalysts under oxygen atmosphere in water medium to produce glycolic acid. In specific embodiments, the reaction is carried out at 120-200° C. with an oxygen pressure of 0.5-4.0 MPa. In certain embodiments, the cellulosic biomass material is selected from the group consisting of cellulose, wood pulp, cotton, starch, lignin, bagasse, grass, glucose, fructose, cellobiose, and sucrose.

In some embodiments of the invention, the molybdenum-containing acidic catalyst is selected from the group consisting of heteropoly acids, heteropolyacid salts, isopoly acids, isopoly acid salt, molybdic acid, molybdenum trioxide, molybdenum dioxide, molybdenum monoxide, complex metal oxides containing molybdenum, and a combination thereof.

In certain embodiments, the heteropoly acid or heteropolyacid salt is represented by the chemical formula $H_w A_x Mo_y O_z$, where A represents one element selected from the group consisting of P, As, Si, Ge, Ce, Th, Mn, Ni, Te, I, Co, Ga, and Fe. In specific embodiments, the heteropoly acid or heteropolyacid salt are selected from the group consisting of $H_3PMo_{12}O_{40}$, $H_3AsMo_{12}O_{40}$, $H_4SiMo_{12}O_{40}$, $H_4GeMo_{12}O_{40}$, $H_8CeMo_{12}O_{42}$, $H_8ThMo_{12}O_{42}$, $H_7PMo_{11}O_{39}$, $H_7AsMo_{11}O_{39}$, $H_8GeMo_{11}O_{39}$, $H_3MnMo_9O_{32}$, $H_6NiMo_9O_{32}$, $H_6TeMo_6O_{24}$, $H_6IMo_6O_{24}$, $H_3[CoMo_6O_{24}H_6]$, $H_3[GaMo_6O_{24}H_6]$, $H_3[FeMo_6O_{24}H_6]$, $H_6P_2Mo_{18}O_{62}$ and $H_6As_2Mo_{18}O_{62}$, and a combination thereof. In certain embodiments, the isopoly acid is represented by the chemical formula $H_wMo_yO_z$. In some embodiments, the isopoly acid is selected from the group consisting of $H_2Mo_6O_{19}$, $H_6M_7O_{24}$, $H_4Mo_8O_{26}$, $H_{10}Mo_{12}O_{41}$, $H_2Mo_2O_7$, $H_8Mo_{10}O_{34}$, $H_2Mo_3O_{10}$, $H_4Mo_5O_{17}$, $H_2Mo_2O_7$, $H_8Mo_{36}O_{112}$, $H_2Mo_5O_{16}$, and a combination thereof.

In particular embodiments of the invention, methods are further defined as comprising the steps of hydrolysis of cellulose to glucose, isomerization of glucose to fructose, dehydration or fragmentation of hexoses, oxidation of shorter carbohydrates produced, or a combination thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

I. Definitions

Figure 1:
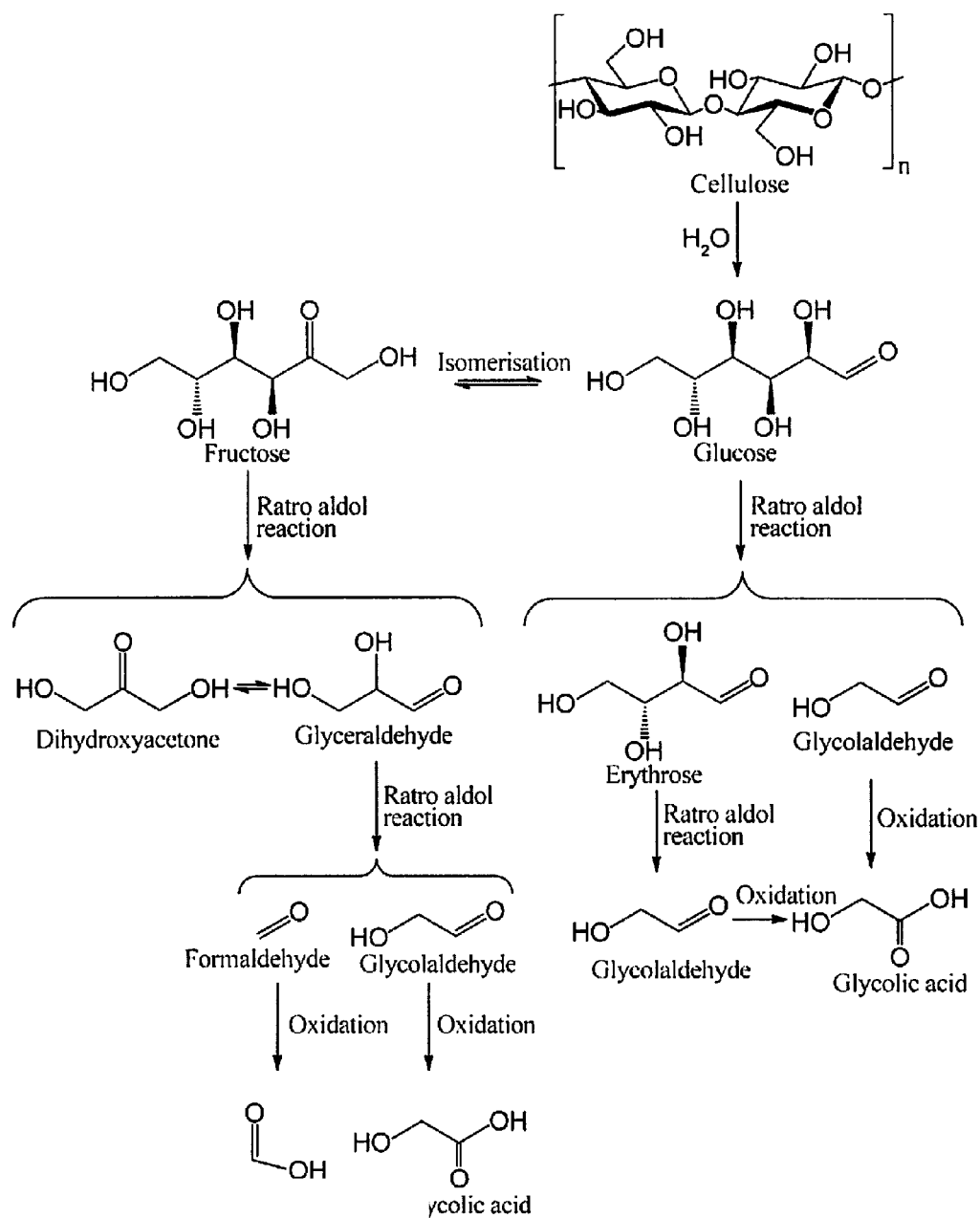
FIG. 1 illustrates an exemplary reaction pathway for the conversion of cellulose to glycolic acid, in certain embodiments of the invention.

As used herein the specification, "a" or "an" may mean one or more. As used herein in the claim(s), when used in conjunction with the word "comprising", the words "a" or "an" may mean one or more than one. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well.

Throughout this application, the term "about" is used to indicate that a value includes the standard deviation of error for the device or method being employed to determine the value.

The term "cellulosic biomass" as used herein refers to the fibrous, woody, and generally inedible portions of plants and in particular refers to cellulose-containing material that is from living or recently living organisms. The skilled artisan recognizes that cellulose is an organic compound with the formula $HO[C_6H_{10}O_5]_nH$, and constituted by polysaccharides comprising linear chains of several hundred to over ten thousand $\beta(1 \rightarrow 4)$ linked D-glucose units, interconnected by hydrogen bond network.

The term "cellulosic biomass material" as used herein refers to matter that is comprised of cellulosic or any subcomponents of cellulose or starch or monosaccharides or disaccharides or polysaccharides.

II. General Embodiments of the Invention

In general embodiments of the invention, there are provided strategies for utilizing Mo-containing acidic catalyst to convert cellulosic biomass to glycolic acid. In some embodiments, there is cellulosic biomass conversion to glycolic acid using Mo-containing heteropoly acids (HPAs), isopoly acids (IPAs) and oxides as catalyst, for example.

A. Cellulosic Biomass

Cellulosic biomass starting materials that may be utilized in the invention include cellulose, starch, lignin, bagasse, grass, glucose, fructose, cellobiose and sucrose. Exemplary sources of cellulosic biomass include agricultural plant wastes, plant wastes from industrial processes (sawdust, paper pulp), or crops grown specifically for fuel production, such as switchgrass and poplar trees, for example.

B. Molybdenum-Containing Catalysts

General embodiments of the present invention concern Mo-containing catalysts, including those having the formula:

In the above formula, A represents P, As, Si, Ge, Ce, Th, Mn, Ni, Te, I, Co, Ga, or Fe. The elements H, A, Mo and O are present in various proportions. For example, H is present in a range between 1 and 10, A is present in a range between 0 and 5; Mo is present in a range between 1 and 50; and, O is present in a range between 1 and 200.

More specific embodiments of the present invention concern Mo-containing catalysts, including those that are heteropoly acids and salts, such as $H_3PMo_{12}O_{40}$, $H_3AsMo_{12}O_{40}$, $H_4SiMo_{12}O_{40}$, $H_4GeMo_{12}O_{40}$, $H_8CeMo_{12}O_{42}$, $H_8ThMo_{12}O_{42}$, $H_7PMo_{11}O_{39}$, $H_7AsMo_{11}O_{39}$, $H_8GeMo_{11}O_{39}$, $H_3MnMo_9O_{32}$, $H_6NiMo_9O_{32}$, $H_6TeMo_6O_{24}$, $H_6IMo_6O_{24}$, $H_3[CoMo_6O_{24}H_6]$, $H_3[GaMo_6O_{24}H_6]$, $H_3[FeMo_6O_{24}H_6]$, $H_6P_2Mo_{18}O_{62}$ and $H_6As_2Mo_{18}O_{62}$.

Additional and/or alternate embodiments of the present invention concern Mo-containing catalysts where A is not present or where x is 0, including those having the formula:

$$H_wMo_yO_z.$$

In the above formula, the elements H, Mo and O are present in various proportions. For example, H is present in a range between 1 and 10, Mo is present in a range between 1 and 50; and, O is present in a range between 1 and 200.

Particular embodiments of the present invention concern Mo-containing catalysts, including those that are isopoly acids and salts, such as $H_2Mo_6O_{19}$, $H_6M_7O_{24}$, $H_4Mo_8O_{26}$, $H_{10}Mo_{12}O_{41}$, $H_2Mo_2O_7$, $H_8Mo_{10}O_{34}$, $H_2Mo_3O_{10}$, $H_4Mo_5O_{17}$, $H_2Mo_2O_7$, $H_8Mo_{36}O_{112}$, $H_2Mo_5O_{16}$.

Other exemplary catalysts suitable in the invention include at least Molybdic acid, $MoO_3 \cdot H_2O$; Molybdenum trioxide, $MoO_3$; Molybdenum dioxide, $MoO_2$; and Molybdenum monoxide, MoO and mixtures of the above oxides.

C. Exemplary Reaction Conditions

Disclosed herein are methods concerning reactions in which cellulosic biomass or cellulosic biomass material is converted to glycolic acid utilizing multi-functional molybdenum-containing acidic catalysts. The following exemplary reaction conditions may be employed.

In specific embodiments, the molar ratio of cellulose (in term of glucose unit):catalyst:water can vary in the following ranges: 1:(0.02-0.5):(500-2000).

In particular embodiments, the reaction is conducted in water under oxygen atmosphere (0.5 MPa-2 MPa) using an autoclave setup. The reaction temperature ranges from about 120° C. to about 200° C. The reaction time ranges from 0.5 h to 3 h.

In some embodiments of the invention, the reaction is carried out at 120-200° C. with an oxygen pressure of 0.5-4.0 MPa. The reaction may be carried out at 120-195° C., 120-190° C., 120-185° C., 120-180° C., 120-175° C., 120-170° C., 120-165° C., 120-160° C., 120-155° C., 120-150° C., 120-145° C., 120-140° C., 120-135° C., 120-130° C., 120-125° C., 125-200° C., 125-195° C., 125-190° C., 125-185° C., 125-180° C., 125-175° C., 125-170° C., 125-165° C., 125-160° C., 125-155° C., 125-150° C., 125-145° C., 125-140° C., 125-135° C., 125-130° C., 130-200° C., 130-195° C., 130-190° C., 130-185° C., 130-180° C., 130-175° C., 130-170° C., 130-165° C., 130-160° C., 130-155° C., 130-150° C., 130-145° C., 130-140° C., 130-135° C., 135-200° C., 135-195° C., 135-190° C., 135-185° C., 135-180° C., 135-175° C., 135-170° C., 135-165° C., 135-160° C., 135-155° C., 135-150° C., 135-145° C., 135-140° C., 140-200° C., 140-195° C., 140-190° C., 140-185° C., 140-180° C., 140-175° C., 140-170° C., 140-165° C., 140-160° C., 140-155° C., 140-150° C., 140-145° C., 145-200° C., 145-195° C., 145-190° C., 145-185° C., 145-180° C., 145-175° C., 145-170° C., 145-165° C., 145-160° C., 145-155° C., 145-150° C., 150-200° C., 150-195° C., 150-190° C., 150-185° C., 150-180° C., 150-175° C., 150-170° C., 150-165° C., 150-160° C., 150-155° C., 155-200° C., 155-195° C., 155-190° C., 155-185° C., 155-180° C., 155-175° C., 155-170° C., 155-165° C., 155-160° C., 160-200° C., 160-195° C., 160-190° C., 160-185° C., 160-180° C., 160-175° C., 160-170° C., 160-165° C., 165-200° C., 165-195° C., 165-190° C., 165-185° C., 165-180° C., 165-175° C., 165-170° C., 170-200° C., 170-195° C., 170-190° C., 170-185° C., 170-180° C., 170-175° C., 175-200° C., 175-195° C., 175-190° C., 175-185° C., 175-180° C., 180-200° C., 180-195° C., 180-190° C., 180-185° C., 185-200° C., 185-195° C., 185-190° C., 190-200° C., 190-195° C., 120° C., 125° C., 130° C., 135° C., 140° C., 145° C., 150° C., 155° C., 160° C., 165° C., 170° C., 175° C., 180° C., 185° C., 190° C., 195° C., or 200° C., for example.

The oxygen pressure for the reaction may be 0.5-4.0 MPa, 0.5-3.5 MPa, 0.5-3.0 MPa, 0.5-2.5 MPa, 0.5-2.0 MPa, 0.5-1.5 MPa, 0.5-1.0 MPa, 0.5-0.75 MPa, 0.75-4.0 MPa, 0.75-3.5 MPa, 0.75-3.0 MPa, 0.75-2.5 MPa, 0.75-2.0 MPa, 0.75-1.5 MPa, 0.75-1.0 MPa, 1.0-4.0 MPa, 1.0-3.5 MPa, 1.0-3.0 MPa, 1.0-2.5 MPa, 1.0-2.0 MPa, 1.0-1.5 MPa, 1.5-4.0 MPa, 1.5-3.5 MPa, 1.5-3.0 MPa, 1.5-2.5 MPa, 1.5-2.0 MPa, 2.0-4.0 MPa, 2.0-3.5 MPa, 2.0-3.0 MPa, 2.0-2.5 MPa, 2.5-4.0 MPa, 2.5-3.5 MPa, 2.5-3.0 MPa, 3.0-4.0 MPa, 3.0-3.5 MPa, 3.5-4.0 MPa, 0.5 MPa, 0.75 MPa, 1.0 MPa, 1.5 MPa, 2.0 MPa, 2.5 MPa, 3.0 MPa, 3.5 MPa, or 4.0 MPa, for example.

EXAMPLES

The following examples are included to demonstrate some embodiments of the invention. It should be appreciated by those of skill in the art that the techniques disclosed in the examples which follow represent techniques discovered by the inventor to function well in the practice of the invention, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the invention.

Example 1

Molybdenum-Containing Acidic Catalysts for Conversion of Cellulosic Biomass to Glycolic Acid In embodiments of the invention, the present invention demonstrates the direct conversion of primitive biomass, cellulose, via successive hydrolysis and selective oxidation in a noble metal-free system.

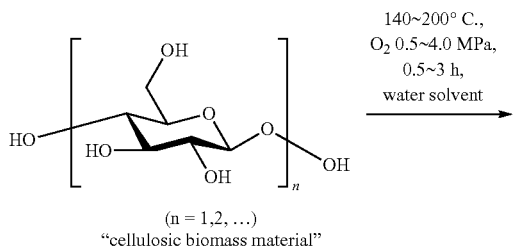

(n = 1,2, ...)
"cellulosic biomass material"

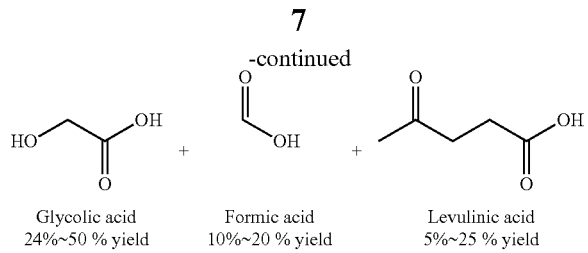

| Glycolic acid | Formic acid | Levulinic acid |
|---|---|---|
| 24%~50 % yield | 10%~20 % yield | 5%~25 % yield |

Instead of using expensive ionic liquid to dissolve the reactant, the inventors utilized water as reaction media and heteropoly acids (HPA) as catalysts. Unlike conventional solid acid catalysts, HPAs are soluble in water and therefore more efficient for catalyzing the reactions of cellulose; on the other hand, they can be recovered in solid form after reaction by distilling out the products and solvent, which is a significant advantage over common volatile liquid acids. In specific aspects of the invention, besides the strong acidity that facilitates the hydrolysis and fragmentation of cellulose, certain HPAs have moderate oxygen activation ability to oxidize the produced carbohydrates. A significant result is achieved by $H_3PMo_{12}O_{40}$ that enables the production of glycolic acid, an important compound widely used in organic synthesis, biodegradable polymer synthesis, skin-care products, industrial rust removal and food processing,[30-31] from commercial α-cellulose powder with a yield of 49.3%. The present invention is the first time to utilize HPAs as multi-functional catalysts for biomass conversion. Interestingly, $H_3PMo_{12}O_{40}$ is even capable of converting raw cellulosic materials in nature, such as bagasse and grass, to glycolic acid in remarkable yields of ~30%.

Four types of Keggin-type HPA including $H_3PW_{12}O_{40}$ (HPW), $H_3PMo_{12}O_{40}$ (HPMo), $H_4SiW_{12}O_{40}$ (HSiW), and $H_4SiMo_{12}O_{40}$ (HSiMo) were tested as catalysts for the conversion of α-cellulose powder at 180° C. in water under 0.6 MPa oxygen using an autoclave setup. The reaction is rather complex with over twenty products generated in total. The major products were identified by high-performance liquid chromatography (HPLC). As summarized in Table 1, all the tested HPA catalysts can convert over 90% cellulose under the reaction conditions, among which HPMo and HSiMo show specific selectivity towards glycolic acid, giving high yields of 49.3% and 46.5%, respectively.

Figure 3:
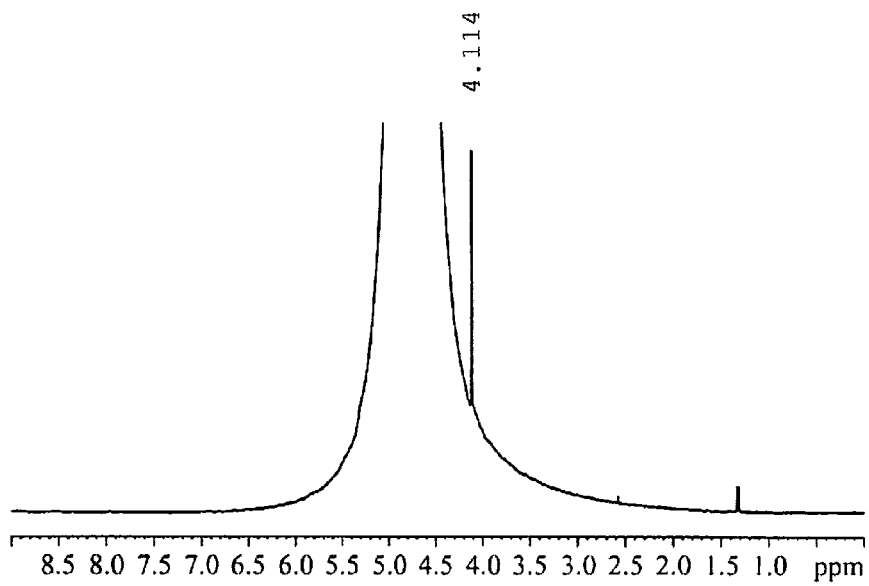
FIG. 3 shows an exemplary NMR spectra of certain isolated products (by HPLC) for the identification of glycolic acid.
Figure 3:
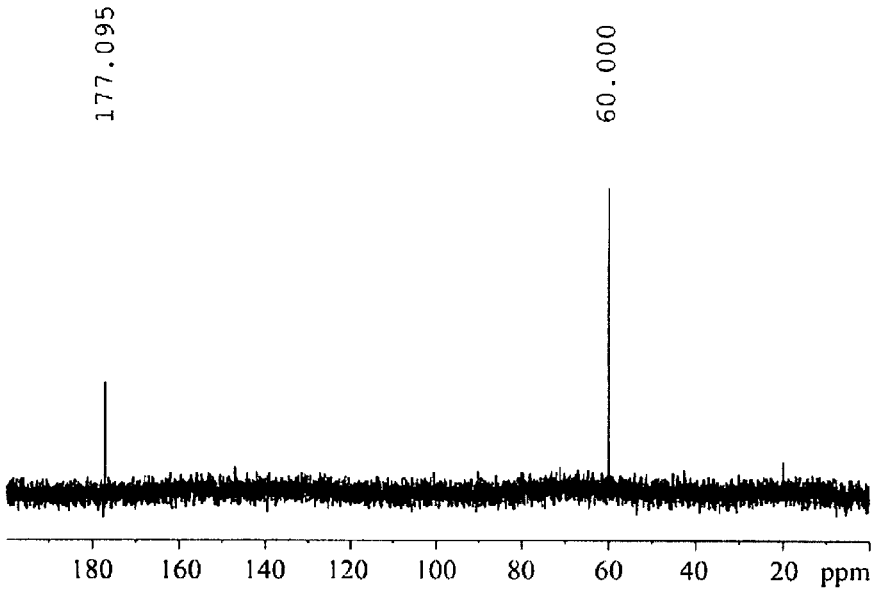

These values were calculated from the isolated product and its purity was confirmed with nuclear magnetic resonance (NMR) spectroscopy (FIG. 3). The two heteropoly tungstic acids (HPW and HSiW), however, show very different catalytic behaviors. They give only a small amount of glycolic acid in yield of <6%, and major products of glucose, levulinic acid and 5-HMF (Table 1), which are formed through the hydrolysis of cellulose, the subsequent isomerization and dehydration processes.[14,15,27] These results indicate that the reaction pathway is mainly determined by the type of addenda atom in HPA catalysts and Mo favors selective oxidation reaction. This is confirmed by the fact that $MoO_3$, which forms molybdic acid in water, also gives remarkable cellulose conversion of 75.7% and glycolic acid yield of 24.5% (Table 1). Basic molybdate $Na_2MoO_4$, however, performs badly with low cellulose conversion of 21%. It is thus demonstrated that molybdate species accounts for the high glycolic acid selectivity while strong acidity is also needed to initialize the reaction by hydrolyzing cellulose.

Step 1: The Hydrolysis of Cellulose to Glucose

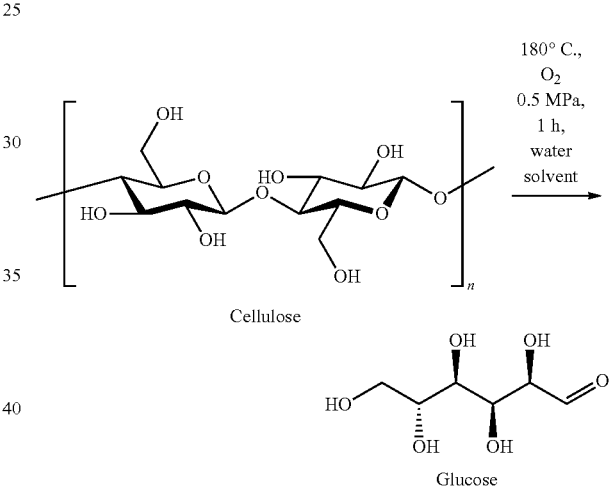

TABLE 1

Yields of the main products derived from cellulose over different catalysts [a]

| | Catalysts | | | | | |
|---|---|---|---|---|---|---|
| Products | HPW | HPMo | HSiW | HSiMo | $MoO_3$ [b] | $Na_2MoO_4$ [b] |
| Glycolic acid | 6.2% | 49.3% | 5.3% | 46.5% | 24.5% | 1.8% |
| Formic acid | 9.7% | 9.6% | 10.9% | 12.6% | 10.8% | 2.2% |
| Acetic acid | 0.5% | 4.0% | 7.8% | 4.7% | 4.6% | 1.6% |
| Glucose | 18.5% | 1.6% | 16.6% | 0.9% | 1.2% | 0.5% |
| Fructose | 4.2% | 5.2% | 3.2% | 4.8% | 4.3% | 0.9% |
| Levulinic acid | 17.7% | 5.5% | 25.4% | 6.8% | 6.9% | 0.2% |
| 5-HMF | 4.6% | 0.1% | 2.6% | 0.5% | 1.2% | 1.0% |
| Others [c] | 4.4% | 7.9% | 5.1% | 6.3% | 5.4% | 1.1% |
| Total yield [d] | 65.7% | 83.3% | 76.8% | 83.2% | 58.7% | 9.2% |
| Cellulose Conversion | 88.3% | 90.5% | 89.6% | 96.2% | 75.7% | 21.0% |

[a] See below for the reaction conditions.
[b] Equivalent molar amount of Mo as for the Mo-containing HPA catalysts.
[c] Other identifiable products include propionic acid, glyceric acid, glycolaldehyde dimer, glycolaldehyde, fromaldehyde.
[d] Total yields of all identified products.

Step 2: The Isomerization of Glucose to Fructose

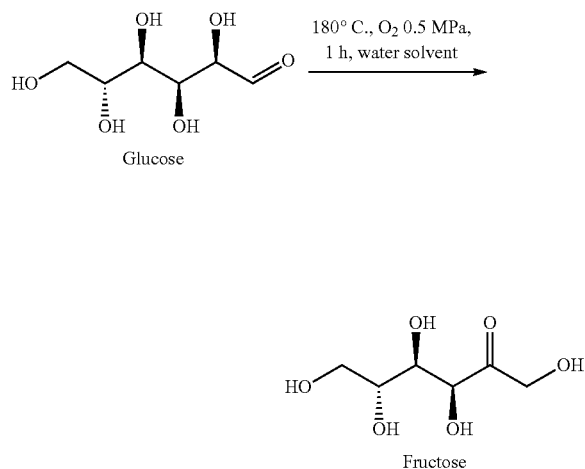

Step 3: The Dehydration or Fragmentation of Hexoses

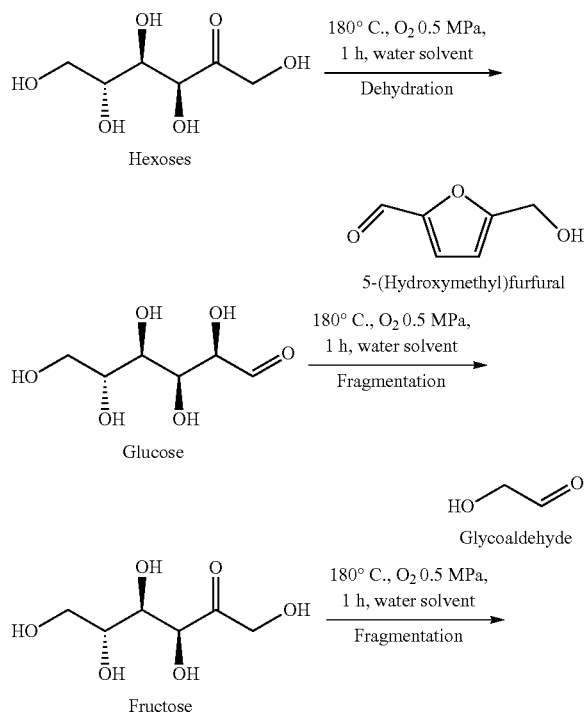

Step 4: The Oxidation of the Produced Shorter Carbohydrates

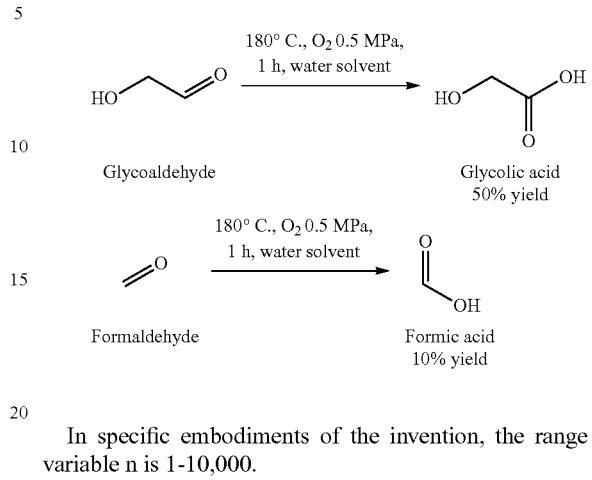

In specific embodiments of the invention, the range of variable n is 1-10,000.

The overall reaction involves a series of successive or parallel steps: the hydrolysis of cellulose to glucose, the isomerization of glucose to fructose, the dehydration or fragmentation of hexoses, and the oxidation of the produced shorter carbohydrates. It was known that glucose and fructose undergo fragmentation in supercritical water to form $C_2$ to $C_4$ carbohydrate products via a retro-aldol reaction, which was also used to explain the formation of lactic acid derivatives from sugars.[18,32,33] In certain aspects, the inventors considered that the Mo-containing HPA-catalyzed reaction proceeds along the pathway depicted in FIG. 1, where the hexoses are fragmented via retro-aldol reactions. Specifically, glucose obtained from the hydrolysis of cellulose undergoes successive retro-aldol reactions to form $C_2$ α-hydroxylaldehyde (glycolaldehyde) that is then converted to glycolic acid through oxidation; in parallel, the isomerization of glucose gives rise to fructose, which can also be converted by retro-aldol reactions through dihydroxyacetone and glyceraldehyde, to glycolaldehyde and formaldehyde, and finally to glycolic acid and formic acid by oxidation.

Step 1: The Hydrolysis of Cellulose to Glucose

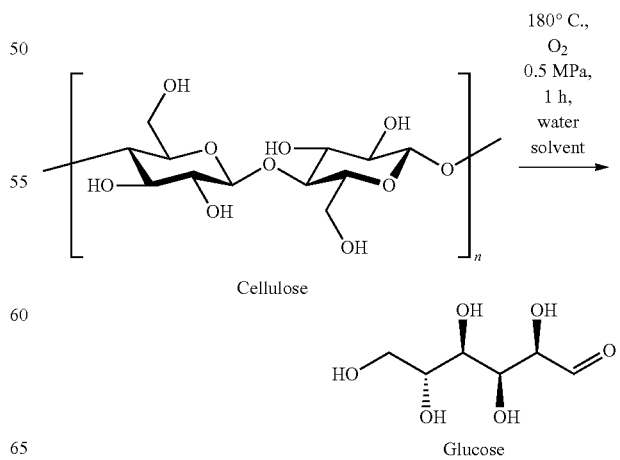

Step 2: The Isomerization of Glucose to Fructose

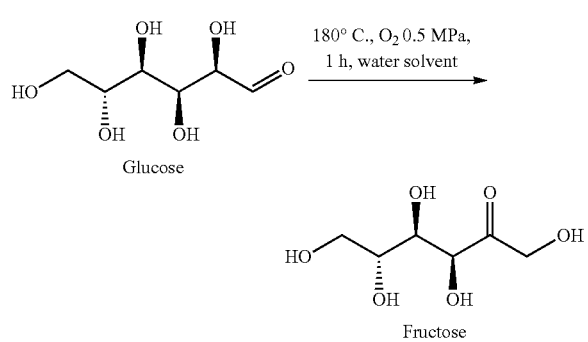

Step 3: The Dehydration or Fragmentation of Hexoses

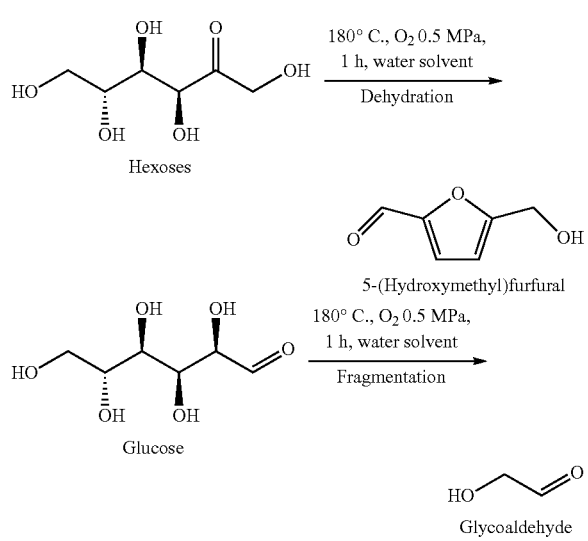

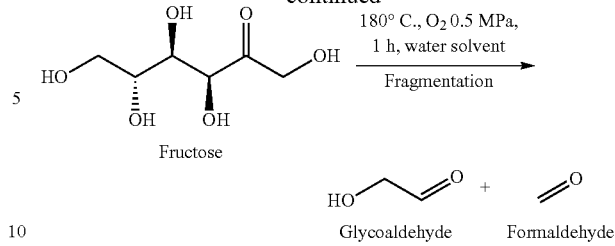

Step 4: The Oxidation of the Produced Shorter Carbohydrates

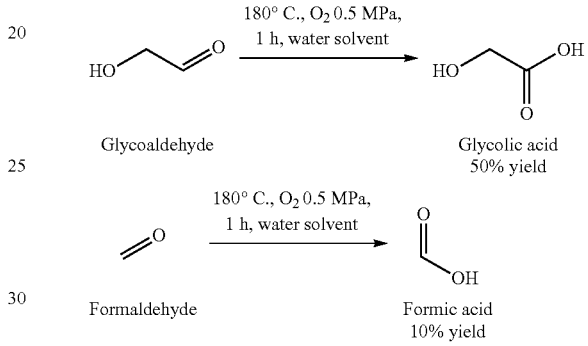

The absence of sugar acids with higher carbon numbers e.g. gluconic acid and erythronic acid in the products implies that the retro-aldol is a faster reaction relative to the oxidation of sugars to sugar acids.

A series of control experiments have been conducted to validate the proposed reaction pathway. Various monosaccharide alcohols, including mannitol, sorbitol, xylitol, erythytol, and glycerol, were firstly tested as reactants for this reaction. None of them were converted under the reaction conditions (Table 2), indicating that HPMo is incapable of catalyzing the oxidation of hydroxyl groups in sugar derivatives.

TABLE 2

Catalytic conversion of various sugar alcohols, sugar acids and glucuronic acid over HPMo catalyst [a]

| Reactants | | Conversion | Glycolic acid Yield | Oxalic acid Yield |
|---|---|---|---|---|
| Mannitol | | <1% | N/A | N/A |
| Sorbitol | | <1% | N/A | N/A |

TABLE 2-continued

Catalytic conversion of various sugar alcohols, sugar acids and glucuronic acid over HPMo catalyst [a]

| Reactants | | Conversion | Glycolic acid Yield | Oxalic acid Yield |
|---|---|---|---|---|
| Xylitol | (structure) | <1% | N/A | N/A |
| Erythritol | (structure) | <1% | N/A | N/A |
| Glycerol | (structure) | <1% | N/A | N/A |
| Ethylene Glycol | (structure) | <1% | N/A | N/A |
| Gluconic Acid | (structure) | <1% | N/A | N/A |
| Glucuronic Acid | (structure) | 88.6% | 25.3% | 3.5% |

[a] The reactions were carried out in a Teflon-lined stainless autoclave (75 mL) at 150° C. for 1 h under 2M Pa $O_2$ with 1000 rpm stirring. 20 mL of $H_2O$, 200 mg of reactant and 0.3 mmol HPMo catalysts were used for the reactions.

Hence, it is unlikely that the C1-C4 products observed in the reaction of cellulose are formed from the direct oxidation decomposition of hexoses. As a monosaccharide acid, gluconic acid showed little conversion either when used as the reactant. It is very interesting to note that under the identical reaction conditions, glucuronic acid, which has the same molecular structure as gluconic acid except for the terminal group (carbonyl vs. hydroxyl), can be nearly completely converted, giving glycolic acid and oxalic acid as the main products (Table 2). These results support the proposed reaction pathway in two aspects: (i) only the sugar derivatives with carbonyl groups that are eligible for a retro-aldol reaction can be converted; (ii) the fragmentation products of glucuronic acid via retro-aldol are glycolaldehyde and glyoxylic acid that can be subsequently oxidized to form glycolic acid and oxalic acid respectively, consistent with the experimental observations.

In some embodiments of the invention, using glucose as reactant leads to higher selectivity of glycolic acid than using fructose. Likewise, in some embodiments polysaccharides containing more glucose segments produce more glycolic acid. To verify this, the inventors conducted reactions using glucose, fructose, cellobiose (disaccharide of glucose) and sucrose (disaccharide of fructose and glucose) as the reactant respectively. The results show that the glycolic acid yields from different reactants follow the order: glucose (42.4%)≈cellobiose (40.0%)>sucrose (35.9%)>fructose (24.6%), in good agreement with the expectation (Table 3).

Step 1: The Hydrolysis of Cellulose to Glucose

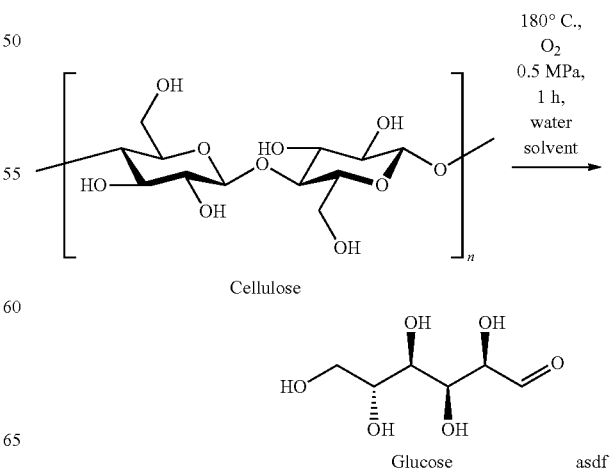

asdf

15
-continued
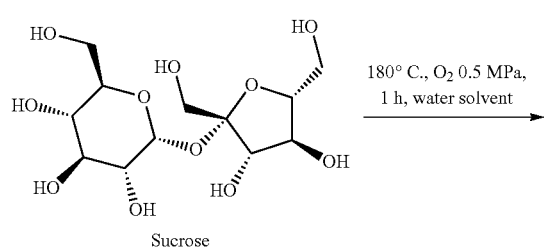
Sucrose
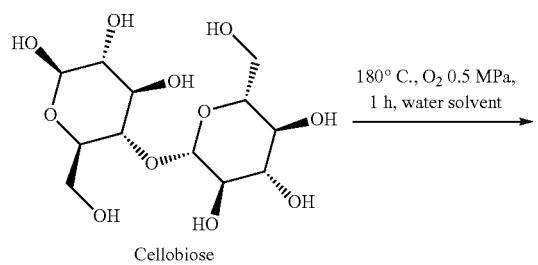
Cellobiose
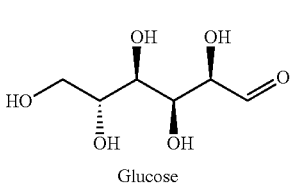
Glucose
Hay or Bagasse $\xrightarrow{\text{180° C., O}_2\text{ 0.5 MPa,} \\ \text{1 h, water solvent}}$ 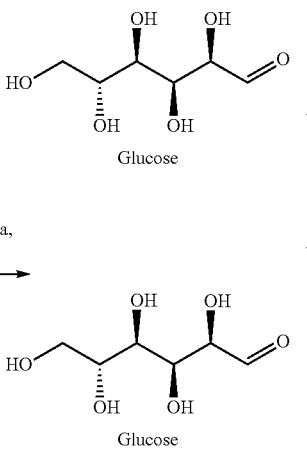
Glucose
Step 2: The Isomerization of Glucose to Fructose
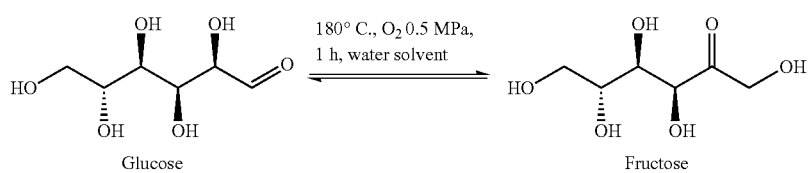 [SMILES: O=C[C@H](O)[C@@H](O)[C@H](O)[C@H](O)CO ; O=C(CO)[C@@H](O)[C@H](O)[C@H](O)CO]
16
Step 3: The Dehydration or Fragmentation of Hexoses
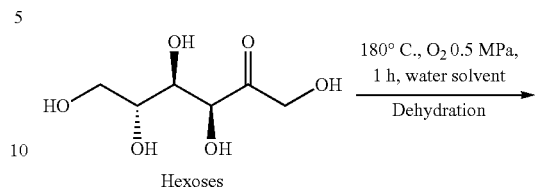
Hexoses
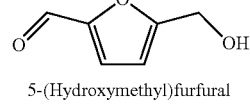
5-(Hydroxymethyl)furfural
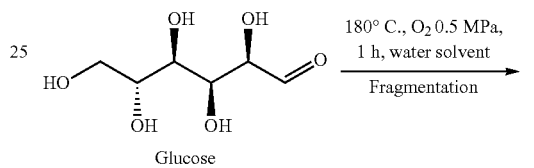
Glucose
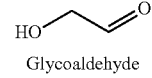
Glycoaldehyde
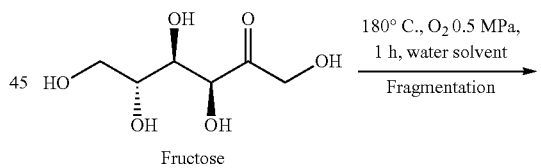
Fructose
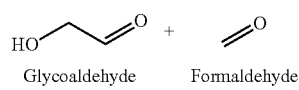
Glycoaldehyde + Formaldehyde Step 4: The Oxidation of the Produced Shorter Carbohydrates

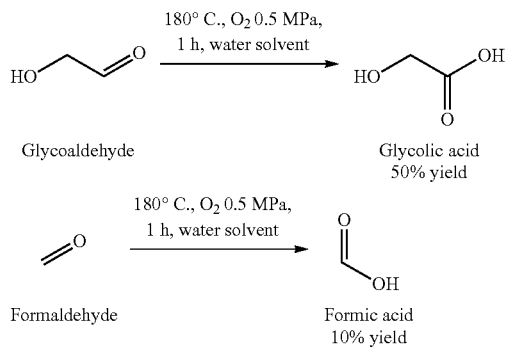

TABLE 3

Yields of all the identified products from the conversion of different sacchariferous reactants over HPMo catalyst

| Products | Reactants | | | | | | |
|---|---|---|---|---|---|---|---|
| | Glucose | Fructose | Cellobiose | Sucrose | Cellulose | Bagass | Hay |
| Glycolic acid | 42.4% | 24.6% | 40.0% | 35.9% | 24.2% | 32.2% | 27.9% |
| Formic acid | 14.6% | 12.6% | 14.1% | 13.0% | 5.6% | 10.1% | 8.4% |
| Acetic acid | 5.6% | 6.3% | 5.0% | 3.9% | 2.9% | 10.9% | 6.7% |
| Glucose | 4.3% | 7.6% | 5.2% | 3.3% | 1.0% | 1.2% | 3.9% |
| Fructose | 11.3% | 4.6% | 13.7% | 7.9% | 2.1% | 4.7% | 4.7% |
| Levulinic acid | 7.4% | 8.8% | 7.6% | 3.3% | 1.5% | 5.8% | 4.9% |
| 5-HMF | 1.0% | 2.0% | 1.4% | 0.5% | 0.9% | 0.8% | 0.6% |
| Propionic acid | 2.4% | 1.1% | 0.0% | 13.7% | 4.0% | 1.4% | 5.1% |
| Glyceric acid | 6.7% | 23.3% | 6.2% | 14.5% | 3.0% | 4.6% | 5.1% |
| Glycolaldehyd | 0.2% | 0.2% | 0.3% | 0.1% | 0.0% | 0.4% | 0.3% |
| Glycolaldehyd | <0.1% | <0.1% | <0.1% | <0.1% | 0.5% | <0.1% | <0.1 |
| Formaldehyde | 0.2% | 0.3% | 0.1% | 0.3% | 1.5% | 0.2% | 0.2% |
| Total yield | 91.8% | 86.6% | 93.7% | 96.1% | 47.2% | 72.4% | 67.8% |
| Reactant | 95.7% | 95.4% | 100% | 100% | 51.2% | 91.7% | 80.1% |

*a* Typical conditions described in experimental section were employed except for the reaction temperature. These reactions were conducted at 150° C.
*b* 0.025 mmol of HPMo catalyst was used.

Accordingly, different reactants produced glyceric acid, which is an oxidative byproduct from the retro-aldol fragmentation of fructose (FIG. 1), with different yields in the opposite order (Table 3). These results strongly support the exemplary reaction pathway and also demonstrate that the isomerization between glucose and fructose is slow under the current reaction conditions. To provide further evidence for this retro-aldol directing reaction pathway, in another parallel experiment, the inventors intentionally decreased the reaction rate by using only one twelfth of the original amount of HPMo catalyst, in order to capture the proposed reaction intermediates. Although some of the expected intermediates such as erythrose, dihydroxyacetone and glyceraldehyde were not detected, possibly because of their instability, formaldehyde and glycoaldehyde were clearly identified in the products by HPLC, which are formed via retro-aldol reaction from fructose and glucose respectively (FIG. 1 and Table 3). Based on all the above results, the inventors concluded that the conversion of cellulose by HPA catalysts is dependent on the type of polyatom. Like other Brönsted acids in previous reports,[34] tungsten-based HPAs favor the dehydration of the sugars and thus mainly produce levulinic acid and 5-HMF. Molybdenum-based HPAs, however, show special ability to facilitate the fragmentation of monosaccharides and moderate activity for the subsequent oxidation reactions, leading to high selectivity towards glycolic acid.

Figure 2:
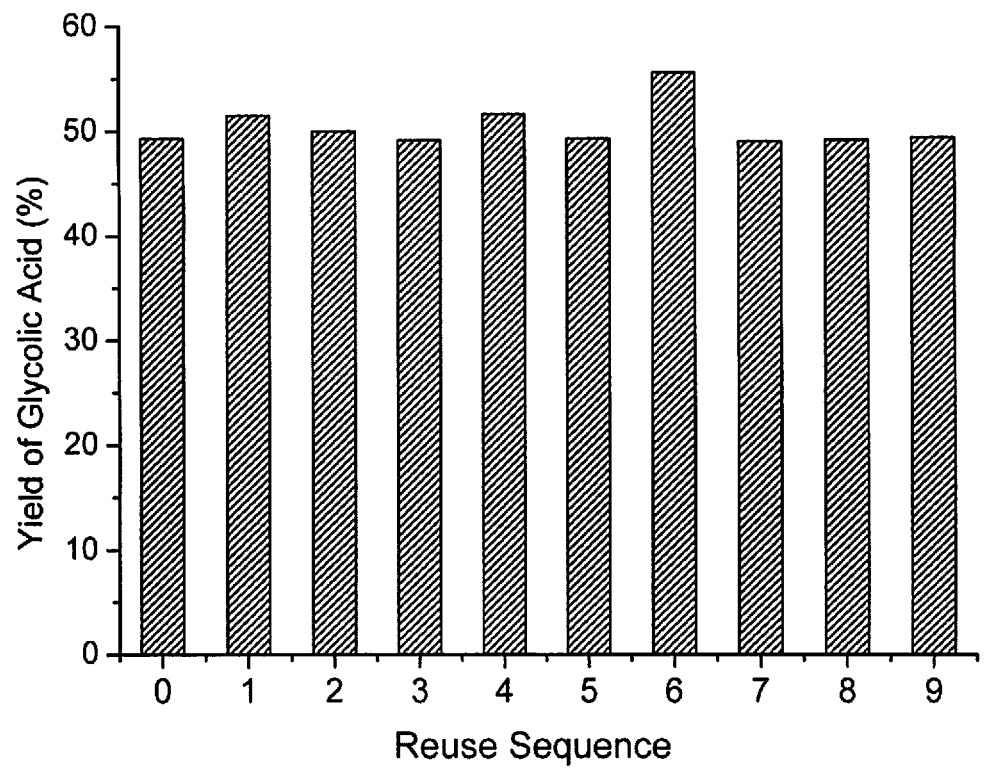
FIG. 2 shows glycolic acid yields in sequential cellulose conversion reactions over HPMo catalyst.

The reusability of HPMo catalyst for cellulose conversion was also investigated. After each reaction cycle, the products and catalyst in liquid phase were firstly separated from the unreacted cellulose by filtration. Water was then removed by low-temperature rotary evaporation. Methanol was added to react with the glycolic acid and other acids to form methyl esters which can be easily collected by vacuum distillation. The residual solid material was hydrothermally treated with oxygen to completely decompose the remaining trace amount of sugars, e.g. glucose and fructose, so as to obtain clean HPMo catalyst for the next reaction run. As indicated in FIG. 2, HPMo shows constant catalytic performance during nine reaction runs with stable yield of glycolic acid of ~50%. The easy recovery and good reusability makes HPA catalysts better candidates for practical applications as compared to the volatile and corrosive liquid acids.

Previous studies have pointed out that cellulose conversion efficiency may be highly dependent on the form of the starting material and special pre-treatments (e.g., ball milling or ultrasonic processing) are usually necessary to achieve effective conversion.[35-38] In this sense, it is worth highlighting that besides the commercial cellulose fibers that are purified "chemicals", HPMo can also catalyze the conversion of "raw" cellulosic biomass. For example, the inventors used bagasse and hay without any treatment except drying as the starting materials for the reaction, and found that they can both be converted to glycolic acid with high selectivity. Assuming that they are comprised of 100% cellulose, the glycolic acid yields are calculated to be 32.2% and 27.9% for bagasse and hay, respectively (Table 3). These results demonstrate the general applicability of HPMo for directly converting various types of crude cellulosic biomass. Notably, few studies have reported so efficient catalytic production of value-added chemicals from raw biomass feedstock.[29,39]

In summary, Mo-containing HPAs prove to be effective catalysts for the conversion of various cellulosic biomasses. Their strong Brönsted acidity facilitates the hydrolysis of cellulose while the moderate oxidative activity allows selective oxidation of the aldehyde groups in the fragmentation products. Among a large number of parallel competing reactions, successive retro-aldol reactions dominate the fragmentation of monosaccharides generated from cellulose hydrolysis, resulting in high selectivity towards glycolic acid. Given that the reactions are conducted in water with little restriction on the types of starting materials, the finding of this work provides a new cost-effective and eco-benign route for biomass conversion, where HPAs combining the merits of homogeneous and heterogeneous catalysts play a crucial role.

Experimental Embodiments

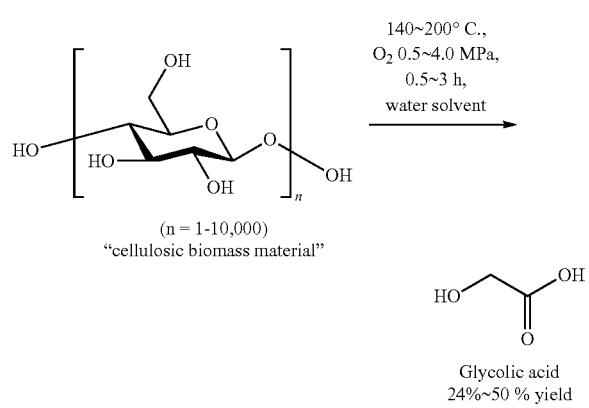

The catalytic reactions of cellulose were carried out in a Teflon-lined stainless autoclave (75 mL) at 180° C. for 1 h under 0.6 M Pa $O_2$ with 1000 rpm stirring. Typically, the reaction mixture comprises 20 mL of $H_2O$, 200 mg of α-cellulose powder (containing 1.23 mmol glucose units), and 0.3 mmol of HPA catalyst. In the reactions of other sacchariferous substrates, a fixed amount (200 mg) of reactant was used. After reaction, the remaining cellulose in the reaction system was collected by centrifugation and its mass was measure for calculating the cellulose conversion. The supernatant liquid was analysed by HPLC (Agilent, 1260 infinity Quaternary System) equipped with RI and UV detectors, and a Waters Shodex SUGAR SH-1011 column (8×300 mm) with 0.05 M $H_2SO_4$ aqueous solution as a mobile phase at 40° C. Quantification of products was carried out by HPLC using an external standard method. Calibration was done by analysing a series of standards covering the concentration range of interest. The peak for each component is integrated and the peak area is plotted against concentration to give a calibration curve. The concentrations of the major products are determined from the calibration curves and used for calculating the yields. The HPLC-purified glycolic acid was dissolved in 0.5 mL of deuterium oxide ($D_2O$) for NMR characterization on a Bruker 500 MHz SB liquid NMR spectrometer operating at 500 and 125 MHz for $^1H$ and $^{13}C$, respectively.

Chemicals List

All chemicals were used as obtained without further purification.

α-Cellulose fiber powder (Sigma), D-(+)-Glucose (Sigma-Aldrich), D-Fructose (SCRC), Sucrose (SCRC), D-(+)-Cellobiose (≥99% Fluka), $H_3PMo_{12}O_{40}$ (Sigma-Aldrich), $H_4SiMo_{12}O_{40}$ (Aldrich), $H_3PW_{12}O_{40}$ (Sigma-Aldrich), $H_4SiW_{12}O_{40}$ (Aldrich), $MoO_3$ (99.5% Sigma-Aldrich), $Na_2MoO_4$ (99.5% Sigma-Aldrich), D-Mannitol (Fisher), D-Sorbitol (98+% ACROS), Xylitol (SCRC), Erythritol (99% Aladdin), Glycerol (99.7% Fisher), Ethylene glycol (99.8% Sigma-Aldrich), D-gluconic acid (99% SCRC), D-Glucuronic acid (98% ACROS), Oxalic acid (99.9% Sigma-Aldrich), Glycolic acid (99% J&K CHEMICA), DL-glyceraldehyde (≥90% Sigma), D-(−)-Erythrose (75% Sigma), Formaldehyde (37 wt % in $H_2O$ Aldrich), Formic acid (37 wt % in $H_2O$ Sigma-Aldrich), Acetic acid (99.9% Fisher), Propionic acid (≥99.5% Fisher), Levulinic acid (98%, Aldrich), Glyceric acid (SCRC), 5-(Hydroxymethyl) furfural (≥99% SAFC), Glycolaldehyde dimer (Aldrich), Methanol (99.8% Sigma-Aldrich), Methyl glycolate (Aldrich), 1,3-Dihydroxyacetone dimer (97% Aldrich), Glyoxylic acid (98% Aldrich), Glyoxal solution (40% in $H_2O$, Sigma-Aldrich), Lactic acid (85% ACROS), Succinic acid (99.5% XL).

Exemplary Preparation of Grass and Bagasse Feedstock for Reactions

From hay, one dries collected grass at least at about 120° C., and the grass may be reduced to small pieces. From bagasse, one can obtain sugar cane, crush it, wash it with water and dry it at least at about 120° C., and the sample may be further processed to produce smaller pieces.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS AND PATENT APPLICATIONS

US Patent Application Publication No. 20110257448
US Patent Application Publication No. 20110009614

PUBLICATIONS

[1] A. Carroll, C. Somerville, *Annu. Rev. Plant Biol.* 2009, 60, 165.
[2] A. J. Ragauskas, C. K. Williams, B. H. Davison, et al., *Science* 2006, 311, 484.
[3] A. E. Farrell, R. J. Plevin, B. T. Turner, et al., *Science* 2006, 311, 506.
[4] H. Danner, R. Braun, *Chem. Soc. Rev.* 1999, 28, 395.
[5] G. W. Huber, S. Iborra, A. Corma, *Chem Rev* 2006, 106, 4044.
[6] A. Corma, S. Iborra, A. Velty, *Chem Rev* 2007, 107, 2411.
[7] M. Mascal, E. B. Nikitin, *Angew. Chem.-Int. Edit.* 2008, 47, 7924.
[8] A. Corma, O. de la Torre, M. Renz, et al., *Angew. Chem.-Int. Edit.* 2011, 50, 2375.
[9] P. Gallezot, *Chem. Soc. Rev.* 2012, 41, 1538.
[10] N. Yan, C. Zhao, C. Luo, et al., *J Am Chem Soc* 2006, 128, 8714.
[11] J. Z. Zhang, X. Liu, M. N. Hedhili, et al., *Chem Cat Chem* 2011, 3, 1294.
[12] P. Gallezot, N. Nicolaus, G. Fleche, et al., *J. Catal.* 1998, 180, 51.
[13] S. Biella, L. Prati, M. Rossi, *J. Catal.* 2002, 206, 242.
[14] H. B. Zhao, J. E. Holladay, H. Brown, et al., *Science* 2007, 316, 1597.
[15] Y. Roman-Leshkov, J. N. Chheda, J. A. Dumesic, *Science* 2006, 312, 1933.
[16] S. Van de Vyver, J. Thomas, J. Geboers, et al., *Energy Environ. Sci.* 2011, 4, 3601.

[17] J. Geboers, S. Van de Vyver, K. Carpentier, et al., *Green Chem.* 2011, 13, 2167.
[18] M. S. Holm, S. Saravanamurugan, E. Taarning, *Science* 2010, 328, 602.
[19] Y. Roman-Leshkov, M. Moliner, J. A. Labinger, et al., *Angew. Chem.-Int. Edit.* 2010, 49, 8954.
[20] M. Moliner, Y. Roman-Leshkov, M. E. Davis, *Proc. Natl. Acad. Sci. U.S.A.* 2010, 107, 6164.
[21] R. P. Swatloski, S. K. Spear, J. D. Holbrey, et al., *J Am Chem Soc* 2002, 124, 4974.
[22] M. E. Zakrzewska, E. Bogel-Lukasik, R. Bogel-Lukasik, *Chem Rev* 2011, 111, 397.
[23] H. Wang, G. Gurau, R. D. Rogers, *Chem. Soc. Rev.* 2012, 41, 1519.
[24] A. V. Bridgwater, G. V. C. Peacocke, *Renew. Sust. Energ. Rev.* 2000, 4, 1.
[25] N. Ji, T. Zhang, M. Y. Zheng, et al., *Angew. Chem.-Int. Edit.* 2008, 47, 8510.
[26] T. D. Matson, K. Barta, A. V. Iretskii, et al., *J Am Chem Soc* 2011, 133, 14090.
[27] J. Tian, J. H. Wang, S. Zhao, et al., *Cellulose* 2010, 17, 587.
[28] K. Shimizu, H. Furukawa, N. Kobayashi, et al., *Green Chem.* 2009, 11, 1627.
[29] Y. Ogasawara, S. Itagaki, K. Yamaguchi, et al., *Chem Sus Chem* 2011, 4, 519.
[30] R. Datta, in *Kirk-Othmer Encyclopedia of Chemical Technology*, John Wiley & Sons, Inc., 2000.
[31] in *Alpha Hydroxy Acids in Cosmetics*, FDA, CSFAN, 2009.
[32] T. M. Aida, K. Tajima, M. Watanabe, et al., *J. Supercrit. Fluids* 2007, 42, 110.
[33] M. Sasaki, K. Goto, K. Tajima, et al., *Green Chem.* 2002, 4, 285.
[34] C. Moreau, R. Durand, S. Razigade, et al., *Appl. Catal. A-Gen.* 1996, 145, 211.
[35] H. B. Zhao, J. H. Kwak, Y. Wang, et al., *Energy Fuels* 2006, 20, 807.
[36] X. M. Dong, J. F. Revol, D. G. Gray, *Cellulose* 1998, 5, 19.
[37] A. Brandt, J. K. Erickson, J. P. Hallett, et al., *Green Chem.* 2012, DOI:10.1039/C2GC15663F.
[38] J. X. Sun, X. F. Sun, H. Zhao, et al., *Polym. Degrad. Stabil.* 2004, 84, 331.
[39] Z. H. Zhang, Z. B. K. Zhao, *Bioresour. Technol.* 2010, 101, 1111.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of converting cellulosic biomass materials to glycolic acid, comprising the steps of reacting one or more cellulosic biomass materials with molybdenum-containing acidic catalysts under oxygen atmosphere in water medium to produce glycolic acid, wherein the molybdenum-containing acidic catalyst is selected from the group consisting of heteropoly acids, heteropolyacid salts, and isopoly acids, and wherein when the catalyst is a heteropoly acid or heteropolyacid salt it is represented by the chemical formula:

$$H_wA_xMo_yO_z$$

wherein

A is one element independently selected from the group consisting of P, As, Si, Ge, Ce, Th, Mn, Ni, Te, I, Co, Ga, and Fe;

w is 1-10;

x is 0-5;

y is 1-50; and, z is 1-200, and wherein when the catalyst is an isopoly acid it is represented by the chemical formula $H_wMo_yO_z$ wherein w is 1-10;

y is 1-50; and, z is 1-200.

2. The method of claim 1, wherein the reaction is carried out at 120-200° C. with oxygen pressure of 0.5-4.0 MPa.

3. The method of claim 1, wherein the cellulosic biomass material is selected from the group consisting of cellulose, wood pulp, cotton, starch, lignin, bagasse, grass, glucose, fructose, cellobiose, and sucrose.

4. The method of claim 1, wherein the heteropoly acid or heteropolyacid salt is selected from the group consisting of $H_3PMo_{12}O_{40}$, $H_3AsMo_{12}O_{40}$, $H_4SiMo_{12}O_{40}$, $H_4GeMo_{12}O_{40}$, $H_8CeMo_{12}O_{42}$, $H_8ThMo_{12}O_{42}$, $H_7PMo_{11}O_{39}$, $H_7AsMo_{11}O_{39}$, $H_8GeMo_{11}O_{39}$, $H_3MnMo_9O_{32}$, $H_6NiMo_9O_{32}$, $H_6TeMo_6O_{24}$, $H_6IMo_6O_{24}$, $H_3[CoMo_6O_{24}H_6]$, $H_3[GaMo_6O_{24}H_6]$, $H_3[FeMo_6O_{24}H_6]$, $H_6P_2Mo_{18}O_{62}$ and $H_6As_2Mo_{18}O_{62}$, and a combination thereof.

5. The method of claim 1, wherein the isopoly acid is selected from the group consisting of $H_2Mo_6O_{19}$, $H_6M_7O_{24}$, $H_4Mo_8O_{26}$, $H_{10}Mo_{12}O_{41}$, $(H_2Mo_2)_7$, $H_8Mo_{10}O_{34}$, $H_2Mo_3O_{10}$, $H_4Mo_5O_{17}$, $H_2Mo_2O_7$, $H_8Mo_{36}O_{112}$, $H_2Mo_5O_{16}$, and a combination thereof.

6. The method of claim 1, further defined as comprising the steps of hydrolysis of cellulose to glucose, isomerization of glucose to fructose, dehydration or fragmentation of hexoses, oxidation of shorter carbohydrates produced, or a combination thereof.

7. A method of converting cellulosic biomass materials to glycolic acid according to the following reaction scheme:

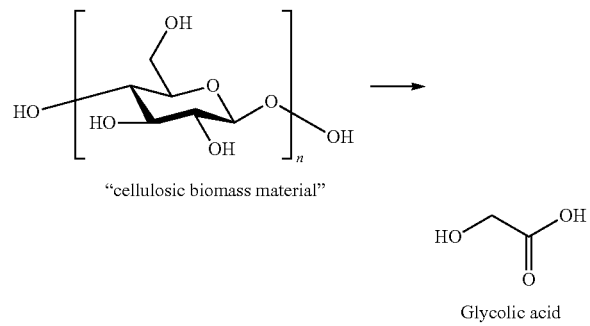

"cellulosic biomass material"

Glycolic acid comprising the steps of:

reacting one or more cellulosic biomass materials with a molybdenum-containing acidic catalyst under oxygen atmosphere in water medium to produce glycolic acid wherein n ranges from 1 to 10,000, wherein the molybdenum-containing acidic catalyst is selected from the group consisting of heteropoly acids, heteropolyacid salts, and isopoly acids, and wherein when the catalyst is a heteropoly acid or heteropolyacid salt it is represented by the chemical formula:

$$H_w A_x Mo_y O_z$$

wherein

A is one element independently selected from the group consisting of P, As, Si, Ge, Ce, Th, Mn, Ni, Te, I, Co, Ga, and Fe;

w is 1-10;

x is 0-5;

y is 1-50; and, z is 1-200, and wherein when the catalyst is an isopoly acid it is represented by the chemical formula $H_w Mo_y O_z$ wherein w is 1-10;

y is 1-50; and, z is 1-200.

8. The method of claim 7, wherein the reaction is carried out at 120-200° C. with oxygen pressure of 0.5-4.0 MPa.

9. The method of claim 7, wherein the cellulosic biomass material is selected from the group consisting of cellulose, wood pulp, cotton, starch, lignin, bagasse, grass, glucose, fructose, cellobiose, and sucrose.

10. The method of claim 7, wherein the heteropoly acid or heteropolyacid salt is selected from the group consisting of $H_3PMo_{12}O_{40}$, $H_3AsMo_{12}O_{40}$, $H_4SiMo_{12}O_{40}$, $H_4GeMo_{12}O_{40}$, $H_8CeMo_{12}O_{42}$, $H_8ThMo_{12}O_{42}$, $H_7PMo_{11}O_{39}$, $H_7AsMo_{11}O_{39}$, $H_8GeMo_{11}O_{39}$, $H_3MnMo_9O_{32}$, $H_6NiMo_9O_{32}$, $H_6TeMo_6O_{24}$, $H_6IMo_6O_{24}$, $H_3[CoMo_6O_{24}H_6]$, $H_3[GaMo_6O_{24}H_6]$, $H_3[FeMo_6O_{24}H_6]$, $H_6P_2Mo_{18}O_{62}$ and $H_6As_2Mo_{18}O_{62}$, and a combination thereof.

11. The method of claim 7, wherein the isopoly acid is selected from the group consisting of $H_2Mo_6O_{19}$, $H_6M_7O_{24}$, $H_4Mo_8O_{26}$, $H_{10}Mo_{12}O_{41}$, $H_2Mo_2O_7$, $H_8Mo_{10}O_{34}$, $H_2Mo_3O_{10}$, $H_4Mo_5O_{17}$, $H_2Mo_2O_7$, $H_8Mo_{36}O_{112}$, $H_2Mo_5O_{16}$, and a combination thereof.

12. The method of claim 7, further defined as comprising the steps of hydrolysis of cellulose to glucose, isomerization of glucose to fructose, dehydration or fragmentation of hexoses, oxidation of shorter carbohydrates produced, or a combination thereof.

* * * * *

UNITED STATES PATENT AND TRADEMARK OFFICE
CERTIFICATE OF CORRECTION

| | |
|---|---|
| PATENT NO. | : 8,846,974 B2 |
| APPLICATION NO. | : 13/859887 |
| DATED | : September 30, 2014 |
| INVENTOR(S) | : Yu Han et al. |

Page 1 of 1

It is certified that error appears in the above-identified patent and that said Letters Patent is hereby corrected as shown below:

In the Claims

In Claim 5 on Column 22, Line 42, delete "$H_2Mo_2)_7$" and insert --$H_2Mo_2O_7$-- therefor.

Signed and Sealed this
Thirtieth Day of December, 2014

Michelle K. Lee
*Deputy Director of the United States Patent and Trademark Office*